(12) United States Patent
Yufa (10) Patent No.: US 8,864,660 B1
(45) Date of Patent: Oct. 21, 2014

(54) SELF-RETAINING VAGINAL RETRACTOR WITH A WEIGHTED SPECULUM

(71) Applicant: Ann Rachel Yufa, Colton, CA (US)

(72) Inventor: Ann Rachel Yufa, Colton, CA (US)

( * ) Notice: Subject to any disclaimer, the term of this patent is extended or adjusted under 35 U.S.C. 154(b) by 149 days.

(21) Appl. No.: 13/694,760

(22) Filed: Jan. 2, 2013

(51) Int. Cl.
*A61B 17/02* (2006.01)
*A61B 1/303* (2006.01)

(52) U.S. Cl.
CPC ............... *A61B 1/303* (2013.01); *A61B 17/02* (2013.01)
USPC .......................................... 600/224; 600/219

(58) Field of Classification Search
USPC ................. 600/201, 202, 210–212, 214, 215, 600/219–224, 226, 235
See application file for complete search history.

(56) References Cited

U.S. PATENT DOCUMENTS

| 350,721 | A | * | 10/1886 | Cooper | 600/224 |
|---|---|---|---|---|---|
| 351,548 | A | * | 10/1886 | Watson | 600/224 |
| 361,087 | A | * | 4/1887 | Schenck | 600/224 |
| 579,625 | A | * | 3/1897 | Willbrandt | 600/224 |
| 761,821 | A | * | 6/1904 | Clark et al. | 600/224 |
| 977,489 | A | * | 12/1910 | Von Unruh | 600/224 |
| 1,194,319 | A | * | 8/1916 | Pretts | 600/224 |
| 1,614,065 | A | * | 1/1927 | Guttmann | 600/235 |
| 2,374,863 | A | * | 5/1945 | Guttmann | 600/224 |
| 5,183,032 | A | * | 2/1993 | Villalta et al. | 600/224 |
| 5,618,260 | A | * | 4/1997 | Caspar et al. | 600/210 |
| 5,681,265 | A | * | 10/1997 | Maeda et al. | 600/219 |
| 5,868,668 | A | * | 2/1999 | Weiss | 600/224 |
| 5,931,777 | A | * | 8/1999 | Sava | 600/213 |
| 6,024,697 | A | * | 2/2000 | Pisarik | 600/224 |
| 6,071,235 | A | * | 6/2000 | Furnish et al. | 600/235 |
| 6,074,343 | A | * | 6/2000 | Nathanson et al. | 600/214 |
| 6,096,046 | A | * | 8/2000 | Weiss | 606/119 |
| 6,120,438 | A | * | 9/2000 | Rizvi | 600/228 |
| 6,196,969 | B1 | * | 3/2001 | Bester et al. | 600/224 |
| 6,280,379 | B1 | * | 8/2001 | Resnick | 600/220 |
| 6,342,036 | B1 | * | 1/2002 | Cooper et al. | 600/224 |
| 7,604,609 | B2 | * | 10/2009 | Jervis | 604/43 |
| 2002/0123667 | A1 | * | 9/2002 | Ouchi | 600/201 |
| 2004/0225196 | A1 | * | 11/2004 | Ruane | 600/220 |
| 2005/0080320 | A1 | * | 4/2005 | Lee et al. | 600/214 |
| 2007/0118022 | A1 | * | 5/2007 | Hutton | 600/219 |
| 2007/0208227 | A1 | * | 9/2007 | Smith et al. | 600/219 |
| 2009/0018399 | A1 | * | 1/2009 | Martinelli et al. | 600/210 |
| 2009/0326331 | A1 | * | 12/2009 | Rosen | 600/224 |
| 2013/0190575 | A1 | * | 7/2013 | Mast et al. | 600/215 |

\* cited by examiner

*Primary Examiner* — Michael T Schaper
*Assistant Examiner* — Amy Sipp (57) ABSTRACT

The present self-retaining vaginal retractor with a weighted speculum comprises the weighted speculum including the speculum blade, speculum projection comprising the teeth for controllable dilation, dilating mechanism, including cables and cable connecting device, left and right pivotable dilating portions, including blades, blade holders and blade holders length adjustment devices, and the handle coupled with the speculum body and including the dilated vaginal opening fixing device comprising the cam and fixation release trigger.

7 Claims, 9 Drawing Sheets

SELF-RETAINING VAGINAL RETRACTOR WITH A WEIGHTED SPECULUM

FIELD OF THE INVENTION

The present invention broadly relates to medical devices for dilating body cavities. Specifically, the present invention is a self-retaining vaginal retractor with a weighted speculum and relates to the gynecological instruments used to dilate the vaginal cavity for vaginal and cervical surgical and/or examination procedures.

BACKGROUND OF THE INVENTION

Numerous patents have been issued on examination and/or surgical gynecological instruments. Devices for retracting the vaginal cavity for gynecological procedures include medical or surgical instruments known variously as speculums, dilators and retractors.

The speculums may be held in place by gravity. Such speculums are known as the weighted speculums. The weighted speculums are well known in gynecology for depressing the posterior (lower) vaginal wall of patients during surgery or other gynecological procedures. However, weighted speculums move, slip and fall onto the floor or even onto the surgeon's feet. They are sometimes slip and fall, because they do not have any additional secure support in the vaginal cavity except the weighted speculum portion inserted into vagina (also known as a weighted speculum blade). The speculum blade is the only one element of the weighted speculum which holds the speculum on the posterior vaginal wall.

As a result, the gynecologist's (surgeon's) is not under control of the weighted speculum position inside vagina during procedure (surgery), considering the possible mobility of the weighted speculum inside vagina [the position of the weighted speculum inside vagina is not securely fixed (retained) during procedure (surgery)].

Also, the surgeon may not control the view required to perform any particular procedure considering the speculum's mobility inside vagina. Heavy weighted speculums come in standard manufactured sizes and sometimes do not fully meet the gynecologist's needs.

All of these factors may affect the quality of the gynecological procedure or surgery, increase procedure time, contribute to the surgeon's frustration, and increase the cost of the surgery or the procedure and the risk of complications.

Another common approach to provide additional and sufficient space for a vaginal surgery is simply to retract the left and right vaginal walls. The most used instruments for such purpose are the manual retractor devises. Generally, the manual retractor device is a two banded (e.g. hook-configured) retractors, each of which is manually (e.g. by the surgeon's assistant) engaged to the middle of the edges of the left and right walls of the patient's vagina and pulled in the opposite to each other direction as far as the left and right vaginal walls may be stretched.

Various improvements have been made to these retractors, making it unnecessary for assistants or nurses to hold them, and also making it possible to provide different degrees of opening with the same equipment.

There are known many medical speculum and retractor devices. For instance, U.S. Pat. No. 7,604,609 to Jervis describes the bendable, reusable medical instruments with improved fatigue life. Generally, it is a needle device which is manufactured from shape memory or pseudo-elastic materials, such as Nickel Titanium alloys. This device may be provided having an initial shape which a doctor may bend to a desired shape. The device may be easily returned to its initial shape after use by heating the device above a predetermined sterilization temperature. This cycle may be repeated during subsequent uses due to the reduced work hardening and enhanced fatigue properties of the Nickel Titanium device.

In accordance with the invention, medical instrument may be manufactured from materials, such as Nitinol alloys, having heat-activated shape memory and/or super-elastic properties with incomplete hysteretic, which provide improved fatigue life. As it is known from invention, the Nitinol alloys, which are exclusively or principally composed of nickel and titanium, exhibit metallurgical properties superior to conventional metals, such as stainless steel and aluminum, in this regard. Martensitic, binary Nitinol, for example, has a stress-strain characteristic which plateaus in a manner permitting unusually large deformations at essentially constant stress through a process of crystallographic twinning. Because of the nature of this twinning, the alloy has comparatively little work hardening which greatly enhances its fatigue properties. Super-elastic Nitinol that does not spontaneously complete its hysteretic cycle after deformation exhibits similar behavior which is due to the formation of stress-induced martensite.

These forms of Nitinol are appropriate for the purposes of making instruments which can be formed during repeated use without adverse effects. A bendable instrument in accordance with the invention may be provided having an initial orientation or shape, a doctor (surgeon) may bend the instrument to a desired shape for use during a procedure, and then the instrument may be returned to its initial shape after use.

For example, a bendable portion of an instrument may be made from a martensitic alloy, that is formed into its initial shape at an elevated temperature while the alloy is in its austenitic phase. During the course of a procedure while at substantially ambient temperatures, the bendable portion may formed into one or more desired shapes. After being used in a procedure, the instrument may be heat sterilized or otherwise heated, thereby automatically returning it to its initial shape such that the user is always presented with a standard shape when the instrument is supplied for subsequent use.

More specifically, the device comprises in general: a vein harvesting hook including a shaft and a working portion and a distal portion of the hook. The shaft includes a small bend and the working portion, which includes an arcuate portion that terminates in a distal tip. During use in a vein harvesting procedure, a surgeon has possibility to bend the hook, for example changing the angle of the bend, or repeatedly adjusting the radius of the arcuate portion to desired shapes suitable for the anatomy encountered during the procedure. After the procedure is completed, the hook may be bent back to its initial shape for reuse.

Also, the described instrument has a weighted speculum, which includes another distal portion and a weighted proximal portion, that are formed to have an initial shape, i.e. a predetermined angle between that another distal and proximal portions. The another distal portion has a contoured arm that is adapted to be inserted into the vaginal canal to facilitate observation and/or access during a gynecological procedure. The proximal portion includes a weight, typically integrally formed in the proximal portion, such that when that another distal portion is inserted into the vaginal canal, the weight pulls the posterior wall down to maintain an opening for accessing or observing the interior of the vagina.

This instrument is expensive, requires special thermal treatments for its adjustability. Another U.S. Pat. No. 6,120,438 to Rezvi describes a posterior vaginal retractor for vaginal surgery or procedure. This device includes a flat plate member, a support member connected to plate member, and an arm member vertically adjustably connected to support member, a speculum member (blade) connected to arm member. The support member includes a first pin member, an elongated slot for slidably receiving pin member therein when arm member is vertically adjustably connected to support member. The speculum member includes a second pin member, and wherein the arm member defines an opening for receiving pin member therein when speculum member is connected to arm member. Also, the support member includes first and second opposed guide elements positioned for slidably receiving arm member therebetween. The arm member includes a handle element for grasping by a user. Arm member further defines an angled portion between opening and slot for enhancing the downward range of movement of arm member and speculum member in relationship with respect to support member. Additionally device comprises a plate member which includes a first triangular plate portion, a second plate portion extending from first plate portion, and a third plate portion extending from first plate portion and in parallel, spaced-apart relationship with second plate portion. The support member is connected to and extends upwardly from the appropriate plate portions.

In operation the first plate portion is positioned under the female patient's buttocks when the patient is on the operating table with legs up. Speculum member is inserted into the patient's vagina, and the position of speculum member is vertically adjusted to a desired fixed position by vertically moving arm member so that speculum member will depress the posterior wall of the vagina to facilitate a vaginal procedure or surgery. Speculum member is connected to arm member by positioning second pin member through opening and by threading nut element onto pin member so that speculum member is fixedly attached to arm member. The first pin member is positioned through elongated slot by slidably positioning arm member between guide elements. The handle element is projected from second side surface and in a direction away from support.

This device does not provide a retraction of vagina in the horizontal direction.

The medical retractor device by U.S. Pat. No. 5,183,032 dilates a vagina in at least three directions. The device generally comprises a supporting box, a mechanism proper, the blades, an opening and closing device. A supporting box comprises two flanges. These flanges are kept apart by spacers. The mechanism proper consists of a sliding member, moving between two flanges. The mechanism also comprises levers and connecting rods. The levers are pivotally mounted between flanges. That portion of the levers which is external to the flanges is in the shape of a circular arc, centered on the articulation point. In this way, when the apparatus is being opened, there is no relative lateral movement between the levers and the flanges and any risk of tearing or pinching the surrounding tissue is thereby obviated.

The device also includes the speculum blades and crankshaft. The blades are fitted perpendicularly to the ends of levers and to the sliding member. The translation of the sliding member induces the rotation of the levers. The sliding member and the levers actuate the blades, which bring about the widening of the vaginal cavity. The crankshaft is pivotable in between flanges. The crank-handle of the crankshaft is engaged in a hole in one end of the sliding member. The rotation of the crankshaft drives the sliding member.

The mechanism properly comprises the levers and connecting rods or links. The levers and connecting rods are symmetrically related to the vertical plane. Some levers are pivotally mounted in between flanges.

The grooved cam or driving means pivots about a shaft, which is positioned by bearings in between flanges and directly linked to a knurled handle control system. The anticlockwise rotation of the cam drives the end of the connecting rods and thereby brings about the lateral movement of the connecting rods. This movement in turn drives the levers, which carry the blades. A sliding member, guided through a pivotally mounted shaft, connected at its lower end to the opening and closing device by a handle. The rotation of the cam directly induces the opening or closing of the sliding member.

This device is very complex and may require some degree of the surgeon's mechanical skills.

The U.S. Pat. No. 6,024,697 discloses a multi-bladed speculum for dilating a body cavity. This speculum includes the blades, the supporting arms, the connections between the supporting arms, the connections between the supporting arms and the blades, the illumination system, and the handles. Each blade is an elongated piece of material, preferably made of a clear hard plastic, with a slight curvature perpendicular to the long axis of the blade and concave to the cavity created by the speculum. The distal end of the blade has a slight curvature parallel to the long axis curved away from the cavity created by the speculum. The proximal end of the blade (the face) is bent in direction to the outside of the speculum. The preferred embodiment has three blades: a top blade, a left blade, and a right blade. The face of each blade consists of two surfaces, an anterior and a posterior face connected to each other at the point where the blade has finished bending to the outside of the speculum. The supporting arms are connected to the anterior and posterior faces in the space between the faces. The device has six supporting members—a left upper arm support, a left lower arm support, a left leg support, a right leg support, a right lower arm support, and a right upper arm support. The left upper arm support is connected to the left lower arm support by a bolt that allows these two supports to pivot about each other, creating a left elbow joint. The portion of the left lower arm support that is proximal to the left elbow joint, and that faces the inside of the speculum. The left upper arm support has a pawl made of a more flexible plastic material that is attached at one end to the left upper arm support. The left leg support is connected to the right leg support by a bolt that allows these two supports to pivot about each other, creating a hinge joint of the left and right leg supports. The portion of the left leg support that is proximal to this hinge joint, and that faces the inside of the speculum. The right leg support also made of a more flexible plastic material that is attached at one end to the right leg support.

Also, the device comprises a left ball-and-socket joint (the "ball" is a ball portion of the left leg support. The socket is formed from a cutaway section of the anterior face of the left blade just anterior and inferior to the ball portion of the left leg support as well as a depression in the posterior face of the left blade just posterior to the ball portion of the left leg support. The left leg support is pivotable) and a right ball-and-socket joint (the "ball" is a ball portion of the right leg support. The socket is formed from a cutaway section of the anterior face of the right blade just anterior and inferior to the ball portion of the right leg support as well as a depression in the posterior face of the right blade just posterior to the ball portion of the right leg support. The right leg support is pivotable too, and this not only allows the ball portion (and thus the right leg support itself) to rotate medially and laterally in the plane between the anterior and posterior faces, but also allows the ball portion of the right leg support to rotate anteriorly).

As it is described in this patent, the speculum has to be inserted as far as it can go, taking care to make sure that, for example, the dilated cervix is located inside the cavity formed by the speculum.

The disadvantage inherent in this retractor is that the device carrying the retractor blades and the parts which serve to support this device inevitably restrict the visibility of and access to the area requiring surgery. Inadequate exposure is a hindrance to the operator and can be particularly dangerous in micro-surgery, where, the surgeon's visibility being limited since he/she must manipulate without visual information in the zone where he moves his hands. It is of extreme importance that the area situated outside the opening should be completely unimpeded.

Additionally, this device is also very complex and may require some degree of the surgeon's mechanical skills.

There many other configurations of the vaginal retractors. For example, the U.S. Pat. No. 6,342,036 describes the self-retaining vaginal retractor. The retractor generally includes a base plate or frame having an inverted, generally U-shape form. The base plate mounts a top vagina retracting blade and a pair of cooperating side vagina retracting blades. The base plate is comprised of a horizontal upper member and a pair of spaced apart, parallel side legs extending perpendicularly downward from the upper member. A horizontal slot is defined through the upper member. A set of snap fasteners are mounted to the back of the upper member near the top of the base. Each of the base legs defines a vertical slot. The top vagina retracting blade and the side vagina retracting blades are secured to the base plate. The top retracting blade is connected to the upper member; and the side retracting blades are connected to the base legs 35. The integral retracting blades each of which has a curved tongue portions and appropriate handle portions. The handle portions define longitudinal slots to receive an adjustably tensionable fastener extending through the appropriate slots of the upper member and legs of the base plate. The tensionable fasteners each of which takes the form of a carriage bolt or similar screw extending through and indexing with a slots of the base plate and a wing nut used to secure the vagina retracting blade in place. The wing nuts are readily adjustable to allow the position of the retracting blades to be adjusted during and following initial deployment of the retractor. Also, device comprises a bag secured to the snap fasteners on the back of the upper member.

This device has a hard frame which limits the movements and positions of the surgeon's hands during gynecological procedure.

Thus, the known devices have some deficiencies, i.e. they are expensive and complex or do not provide an unobstructed access to and reasonably acceptable visibility of the inside vaginal area under gynecological procedure or surgery.

While the mentioned above prior art fulfill their respective, particular objectives and requirements, the mentioned prior art inventions do not disclose, teach and/or suggest the non-complex and non-expensive self-retaining vaginal retractor with a weighted speculum providing non-obstructed good visibility of the dilated body cavity and specifically of the vagina.

Those skilled in the art will readily observe that numerous modifications and advantages of the improved self-retaining vaginal retractor with a weighted speculum may be made while retaining the teachings of the invention.

Thus, the known prior art do not provide the efficient, not expensive, non-complex and convenient device for dilation of the patient vagina according to the present invention substantially departs from the devices of the prior art.

OBJECT AND ADVANTAGES OF THE INVENTION

Accordingly, several objects and advantages of the present invention are to provide the improved self-retaining vaginal retractor with a weighted speculum:

It is an object of the present invention to provide non-expensive self-retaining vaginal retractor with a weighted speculum.

It is another object of the present invention to provide non-complex self-retaining vaginal retractor with a weighted speculum.

It is still an object of the present invention to provide multi-blades self-retaining vaginal retractor with a weighted speculum.

It is further an object of the present invention to provide the self-retaining vaginal retractor with a weighted speculum and controllable dilation of vaginal cavity.

It is still another object of the present invention to provide the multi-blades non-frame-including vaginal retracting device which does not obstruct the movements and positions of the gynecologist's/surgeon's hands during gynecological procedure or surgery.

It is still further object of the present invention to provide the self-retaining vaginal retractor with securely retained position of the weighted speculum, and to provide the unrestricted and unostructed visibility of and access to the vaginal canal for requiring surgical and/or examination gynecological procedure.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

Still, further objects and advantages will become apparent from a consideration of the ensuing description accompanying drawings.

DESCRIPTION OF THE DRAWING

In order that the invention and the manner in which it is to be performed can be more clearly understood, embodiments thereof will be described by way of example with reference to the attached drawings, of which.

It is understood, that these illustrations and drawings are the examples of the improved apparatus configurations and architectures, and those skilled in the art will readily observe that numerous structures, modifications and advantages of the improved apparatus—self-retaining vaginal retractor with a weighted speculum may be made while retaining the teachings of the present invention.

THE DRAWING REFERENCE NUMERALS

1.—a self-retaining vaginal retractor with a weighted speculum;
2.—a vaginal canal;
3.—a female body;
4.—a weighted speculum;
5.—a speculum body;
6.—a speculum blade;
7.—a middle portion;
8—a tubular means;
9—a dilating mechanism;
10.—a swollen portion;
11.—a lower portion;
12.—a speculum projection;
13.—a speculum blade axis;
14.—a middle portion axis;
15.—an upper tubular holder;
16.—a lower tubular holder
17.—a main cable;
18.—a handle projection;
19.—a handle means;
20.—a fixation release trigger;
21.—a vaginal opening;
22.—a lower end of the main cable 17;
23.—an upper end of the main cable 17;
24.—a first end of the left cable 25;
25.—a left cable;
26.—a first end of the right cable 27;
27.—a right cable;
28.—a second end of the left cable 25;
29.—a free end of the left hook 30;
30.—a left hook;
31.—a second end of the right cable 27;
32.—a free end of the right hook 33;
33.—a right hook;
34.—a left dilating portion;
35.—a right dilating portion;
36.—a c; able connecting means
37.—a left knee;
38.—a first aperture;
39.—a left blade holder;
40.—a left blade length adjustment means;
41.—a left blade;
42.—a right knee;
43.—a second aperture;
44.—a right blade holder;
45.—a right blade;
46.—a right blade length adjustment means;
47.—an upper end of the left blade holder 39;
48.—an upper end of the right blade holder 44;
49.—teeth;
50.—a cam;
51.—a pawl;
52.—a spring;
53.—a fixing means;
54.—a screw;
55.—a recess;
56.—a right knee projection;
57.—a first fixing pin;
58.—a third aperture;
59.—handle means extensions;
60.—a second fixing pin;
61.—an auxiliary spring;
62-62—a side view of the improved self-retaining vaginal retractor with a weighted speculum;
63-63—a cross-section of the left blade 41;
64-64—a cross-section of the right blade 45;
65-65—a cross-section of the left blade 41 with the star-grooved shape of the upper end 47 of the left blade holder 39;
66-66—a cross-section of the left knee 41 with the recess 55;
67-67—a cross-section of the right knee 42 with right knee projection 56;
68-68—a cross-section of the left knee 41 with the U-shape configuration;
69-69—a cross-section of the right knee with the straight configuration;
70-70—a cross-section of the left blade length adjustment means 40;
71-7—a cross-section of the middle portion 7 of the speculum body 5;
72-72—a cross-section of the swollen portion 10 of the speculum body 5;
73-73—a cross-section of the right blade holder 44;

74-74—a front cross-sectional view of the coupling of the handle means 19 with the speculum projection 12;

75-75—a top cross-sectional view of the coupling of the handle means 19 with the speculum projection 12;

SUMMARY OF THE INVENTION

In view of the foregoing disadvantages inherent in the known prior art, the present invention provides an improved self-retaining vaginal retractor with a weighted speculum. As such, the general purpose of the present invention, which will be described hereinafter in greater details, is to dilate the vaginal cavity for vaginal and cervical surgical and/or examination procedures.

The improved self-retaining vaginal retractor with a weighted speculum has many of the advantages of the gynecological instruments and many novel features that result in the efficient, convenient and secured dilating of the vaginal canal, which is not anticipated, rendered obvious, suggested or even implied by any of prior art methods and devices for dilating of the vaginal cavity.

This invention, self-retaining vaginal retractor with a weighted speculum, provides the convenient, secured and unobstructed dilated access into vaginal canal for vaginal surgical and/or examination procedures.

To attain this, the present invention generally comprises the weighted speculum comprising the speculum blade, speculum projection including the teeth, dilating mechanism, including cables and cables connecting means, left and right dilating portions, including blades and blade holders length adjustment means, and the handle means coupled with the speculum body and including the dilated vaginal opening fixing means comprising the fixation release trigger.

DESCRIPTION OF THE PREFERRED EMBODIMENTS

With reference now to the drawings, and particularly to FIGS. 1-15B thereof, an improved self-retaining vaginal retractor with a weighted speculum embodying the principles and concepts of the present invention.

Figure 1:
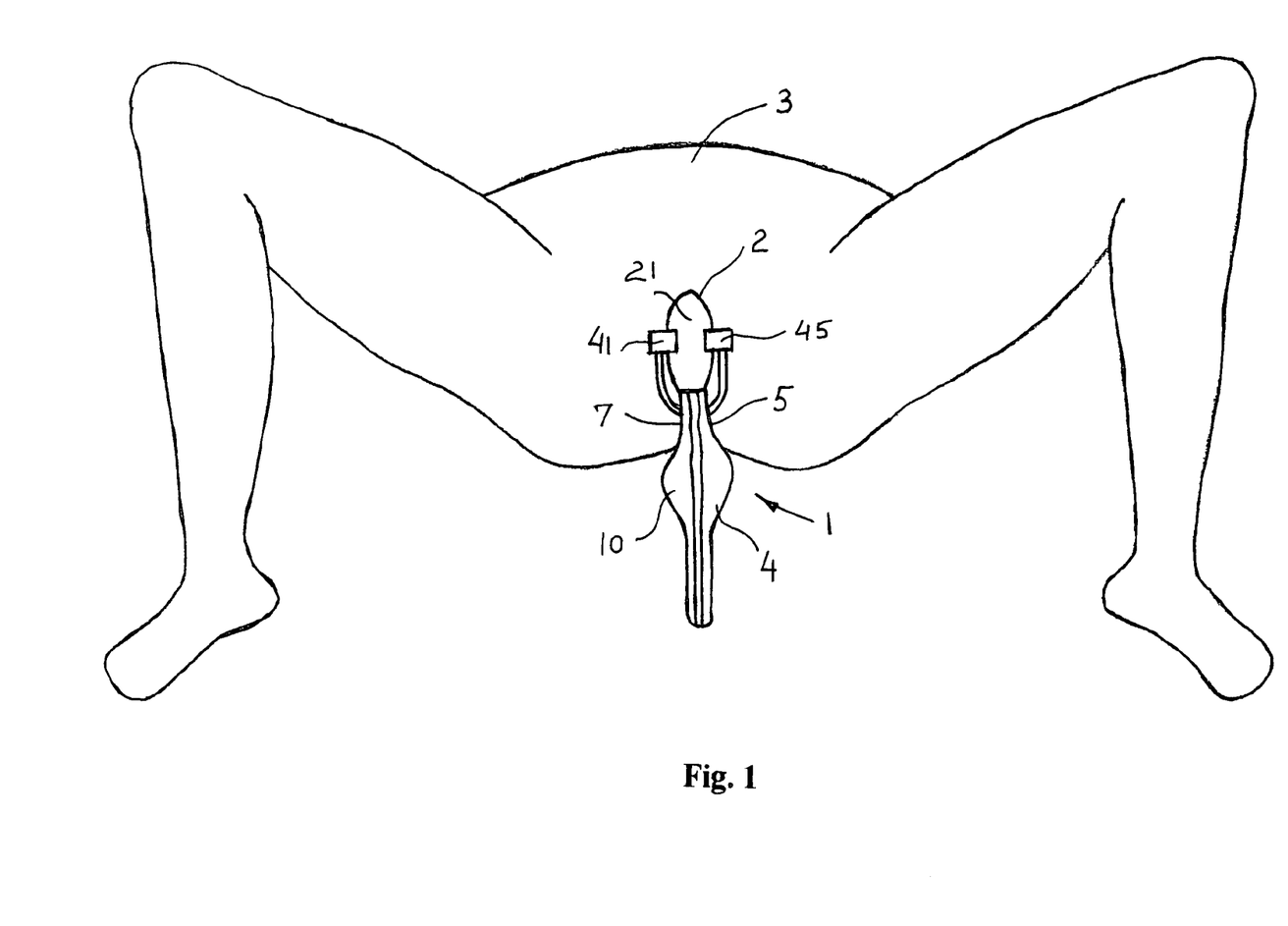
FIG. 1 is a simplified illustration of the improved self-retaining vaginal retractor with a weighted speculum.

In the FIG. 1 is shown the improved self-retaining vaginal retractor with a weighted speculum (herein further may be also mentioned as an "apparatus" or "device") 1 appropriately inserted in the vaginal canal (vaginal cavity) 2 of the female patient's body 3.

Figure 3:
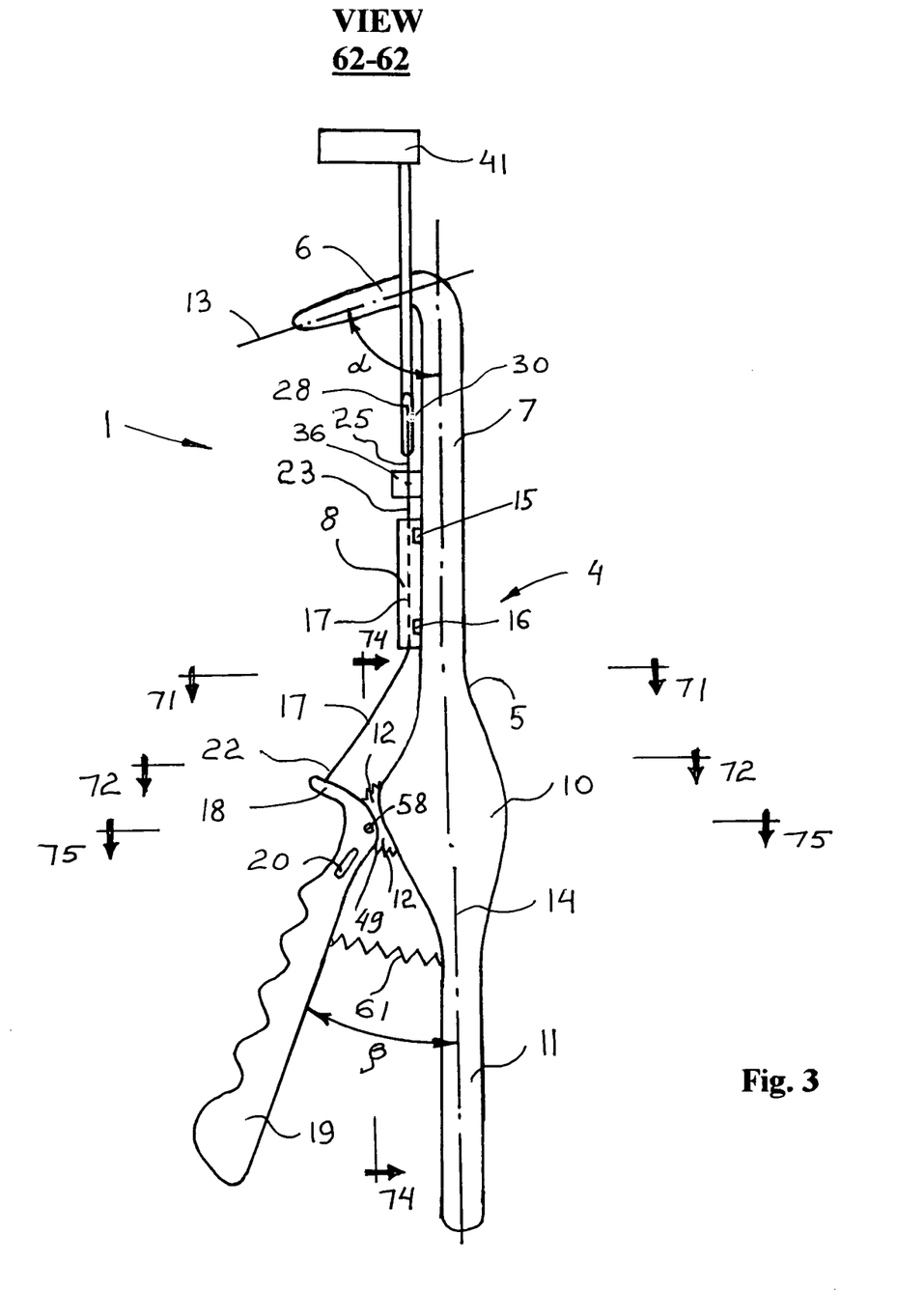
FIG. 3 is a simplified left side view 62-62 of the improved self-retaining vaginal retractor with a weighted speculum.

The improved device 1 includes the weighted speculum 4 (herein further may be also mentioned as "speculum"), comprising the speculum body 5 and speculum blade 6. The speculum body 5 includes the middle portion 7, as it is shown in FIGS. 1 and 3 (see also FIGS. 12A, 12B, 15A). The speculum body 5 also comprises the tubular means 8, the swollen portion 10, used as a weight, and the elongated lower portion 11, also shown in FIGS. 3, 15A (the cross-sectional view of the swollen portion 10 is additionally shown in FIGS. 12B, 15B). {The term "tubular" hereinbelow solely and/or jointly accumulate the meaning, for instance, of the "tube", "pipe", etc., therefore, the use at least one of the terms does not exclude the other meanings for the used term, if otherwise not specified}.

The swollen portion 10 typically integrally formed in the speculum 4 in such manner that when the speculum blade 6 is inserted into the vaginal canal, the swollen portion 10 (as a weight) pulls the posterior vaginal wall down to maintain an opening for accessing or observing the interior of the vagina The speculum body 5 includes the speculum projection 12. The speculum blade 6 bended under predetermined angle "a"

to the middle portion 7 and is adapted to be inserted into the vaginal canal 2 to facilitate observation and/or access during a gynecological procedure or surgery. Specifically, angle "a" is located between the speculum blade axis 13 and the speculum body axis 14, as it is shown in FIG. 3.

Figure 14:
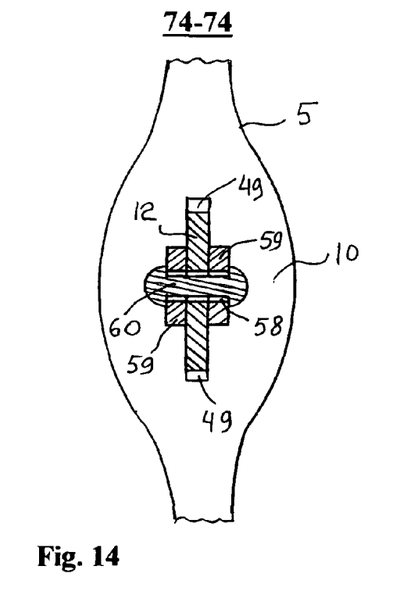
FIG. 14 is a simplified front cross-sectional view 74-74 of the coupling of the handle means with the speculum projection.
Figure 15A:
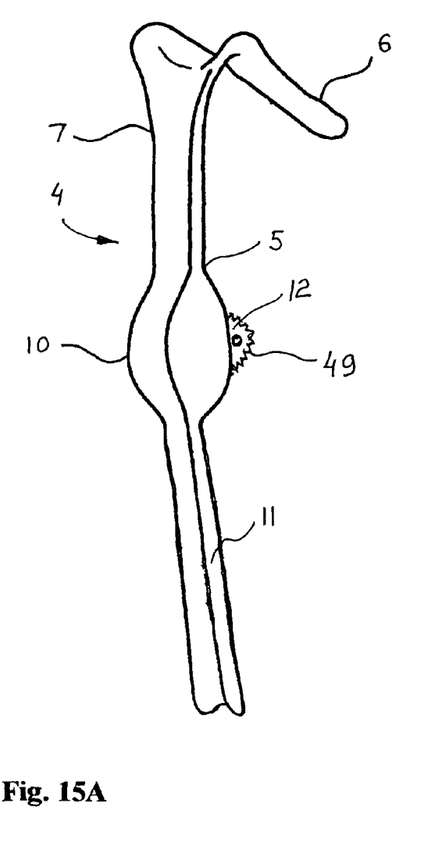
FIG. 15A is a simplified spatial view of the weighted speculum.
Figure 15B:
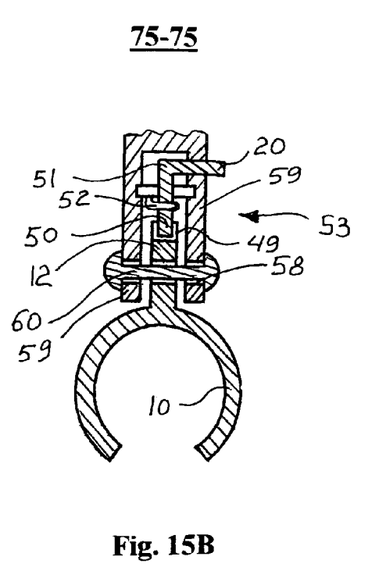
FIG. 15B is a simplified top cross-sectional view 75-75 of the coupling of the handle means with the speculum projection.

The speculum projection 12 may extend from the speculum body 5 (e.g. from the swollen portion 10, as it is shown in FIG. 15B) or can be attached to the speculum body 5 (FIG. 3). The speculum projection 12, for example, can have the semi-circular configuration shown in FIGS. 3, 15A. It should be understandable, that speculum projection 12 can extend from or be attached to the speculum body 5 at any reasonable and convenient place of the speculum body 5 [e.g. at the area of the swollen portion 10 of the speculum body 5 (FIGS. 3, 14, 15A, 15B), etc.].

The speculum body 5 comprises an upper tubular means holder 15 and a lover tubular means holder 16 intended to hold the tubular means 8 (if the tubular means 8 is attached to the speculum body 5), directing the main cable 17. The tubular means 8 is preferred to be extended from the speculum body 5, as it is illustrated in FIG. 15B. It should be understood, that the tubular means holders 15 and 16 (FIG. 3) can extend from or be attached to the speculum body 5 at any reasonable and convenient place of the speculum body 5. The tubular means 8 can be held, for example, by one single tubular holder (not shown) instead of two tubular means holders 15 and 16 (summarizing, by at least one of a plurality of tubular means holders).

The dilating mechanism 9 comprises a main cable 17 which passes through the tabular means 8. The lower end 22 of the main cable 17 is coupled with the handle projection 18 of the handle means 19. The handle means 19 is coupled with the speculum projection 12.

The coupling of the handle means 19 with the speculum projection 12 can be provided by any suitable fixing means, for instance, by the fixing means 53, wherein the fixation is provided by the teeth 49 (FIGS. 3, 14, 15A, 15B) and pawl 51 (FIG. 15B) or the ratchet mechanism (not shown), and wherein the fixation release is provided by the fixation release trigger 20 extended from the pawl 51 in the direction opposite to the location of the cam 50. The fixing means 53 can fix the handle means 19 position at any point in the range of angle "β" (FIG. 3), thereby, providing the controllable width of the vaginal opening 21 (FIG. 1) of the vaginal canal 2.

The upper end 23 of the main cable 17 is coupled by the cable connecting means 36 (FIG. 2) with the first end 24 of the left cable 25 and with the first end 26 of the right cable 27. The second end 28 of the left cable 25 is coupled with the free end 29 of the left hook 30 (FIG. 4) of the left dilating portion 34. The second end 31 of the right cable 27 is coupled with the free end 32 of the right hook 33 (FIG. 5) of the right dilating portion 35. The coupling of the left and right cables with the hooks can be provided by any reasonable and convenient methods, e.g., by knots (not shown), rivets (not shown), welding (not shown), gluing (not shown), etc.

Figure 4:
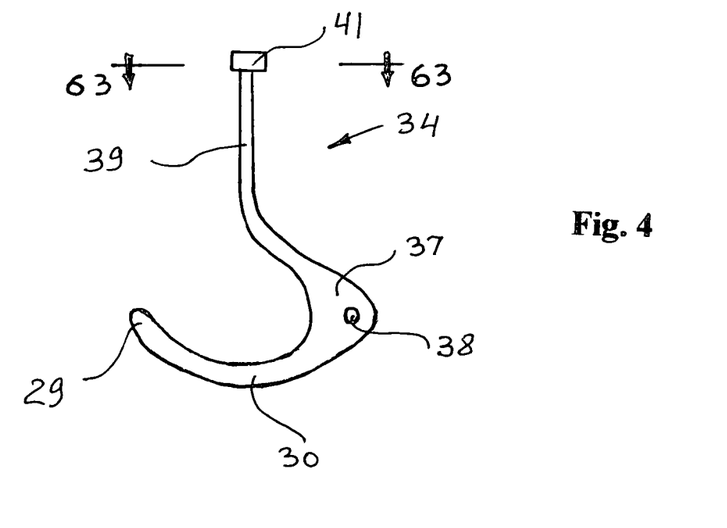
FIG. 4 is a simplified drawing of the left dilating portion of the improved self-retaining vaginal retractor with a weighted speculum.

The left dilating portion 34 also includes a left knee 37, comprising a first aperture 38, a left blade holder 39 and a left blade 41 (FIG. 4). The left dilating portion 34 can comprise a left blade length adjustment means 40 (FIG. 11A).

Figure 5:
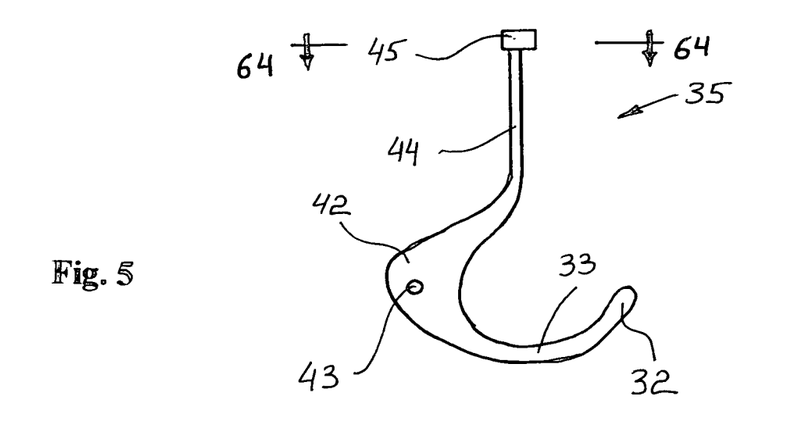
FIG. 5 is a simplified drawing of the right dilating portion of the improved self-retaining vaginal retractor with a weighted speculum.

The right dilating portion 35 also includes a right knee 42, comprising a second aperture 43, a right blade holder 44 and a right blade 45 (FIG. 5). The right dilating portion 35 can comprise a right blade length adjustment means 46 (FIG. 11B) analogous to the left blade length adjustment means 40.

It is understood, that the length adjustment means 40, 46 can be of any reasonable and convenient structure. In FIGS. 11C, 11D is shown, for example, the left blade length adjustment means 40 based on the retractable portions of the left blade holder with the fixing screw (not shown). The right blade length adjustment means 46 can be of the same configuration (not shown). The length adjustment means can be based on the threaded portions (not shown) of the appropriate coupling to each other interrupted threaded (not shown) holder portions of a cylindrical (not shown) configuration, etc.

Figure 11A:
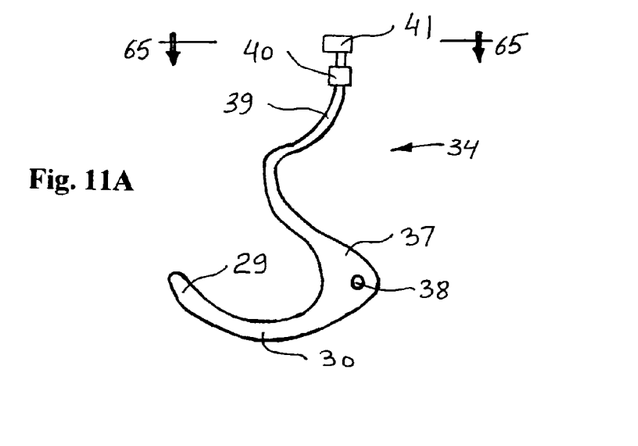
FIG. 11A is a simplified drawing of the left blade holder with the left blade length adjustment means.
Figure 11B:
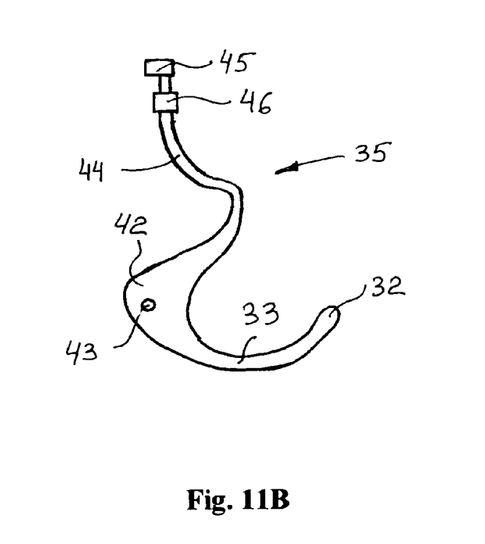
FIG. 11B is a simplified drawing of the right blade holder with the right blade length adjustment means.
Figure 11C:
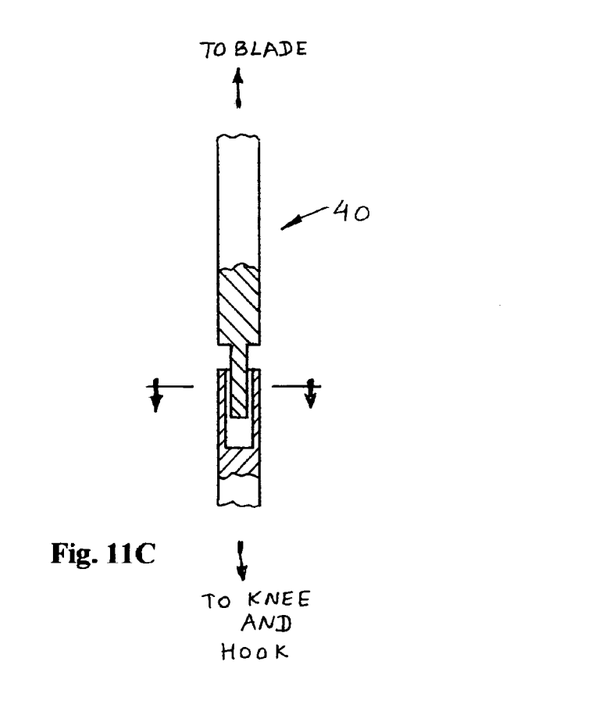
FIG. 11C is a simplified drawing of the variant of the length adjustment means.
Figure 11D:
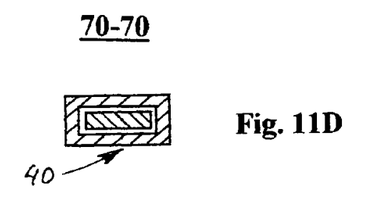
FIG. 11D is a simplified cross-sectional view 70-70 of the length adjustment means.
Figure 12A:
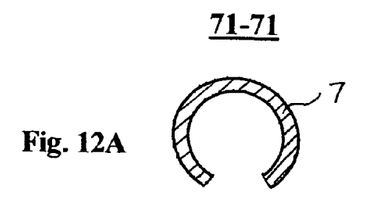
FIG. 12A is a simplified cross-sectional view 71-71 of the middle portion of the speculum.
Figure 12B:
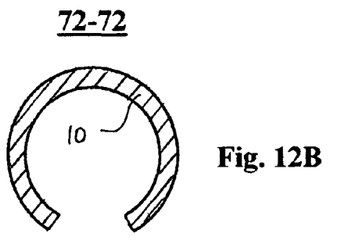
FIG. 12B is a simplified cross-sectional view 72-72 of the swollen portion of the speculum.
Figure 12C:
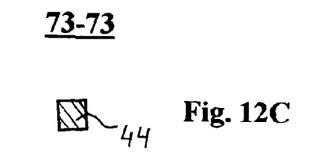
FIG. 12C is a simplified cross-sectional view 73-73 of the right blade holder.
Figure 13:
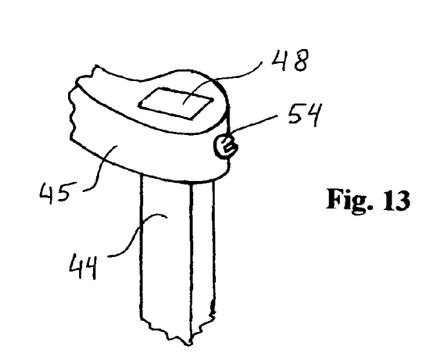
FIG. 13 is a simplified drawing of the coupling of the right blade with the right blade holder.

The left 34 and right 35 dilating portions (as well as their blade holders 39 and 44) can be of configuration shown in FIGS. 4 and 5, but also can be of configuration shown, as an example, in FIGS. 11A and 11B. It should be understandable, that configurations of the dilating portions 34 and 35 can of any reasonable and convenient forms. It is understood that the left 40 and right 46 blade length adjustment means can be identical.

Figures 6A, 6B:
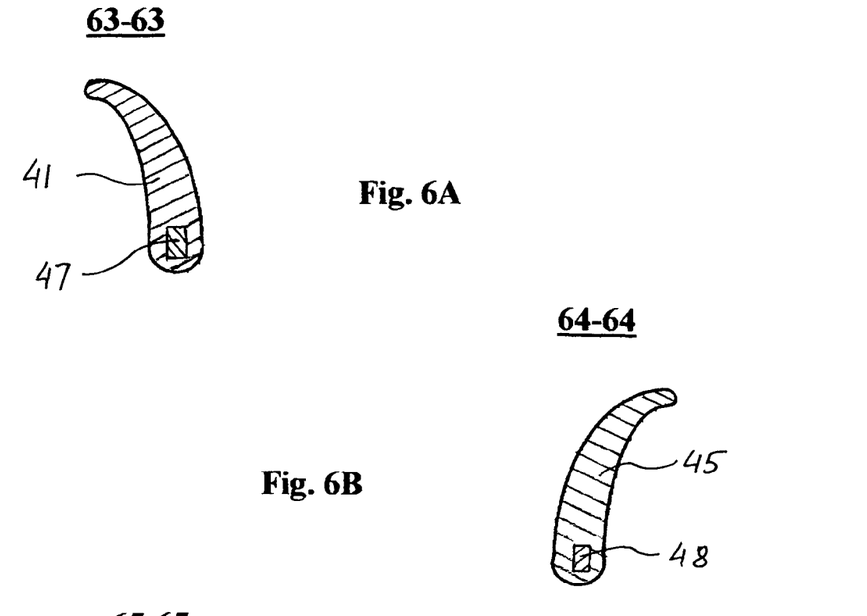
FIG. 6A is a simplified cross-sectional view 63-63 of the left blade.
FIG. 6B is a simplified cross-sectional view 64-64 of the right blade.
Figure 6C:
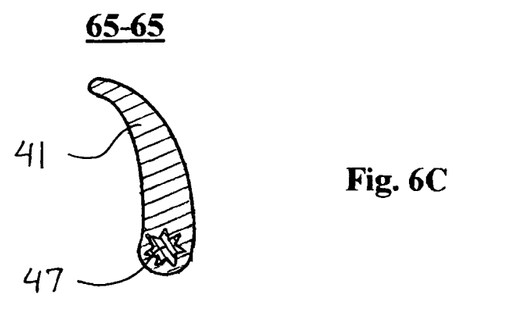
FIG. 6C is a simplified cross-sectional view 65-65 of the left blade with the star-grooved shape of upper end of the left blade holder.

The upper end 47 of the left blade holder 39 can have the square cross-sectional configuration (not shown), rectangular cross-sectional configuration (FIG. 6A) or can have a star cross-sectional configuration (star-grooved shape of the upper end 47 of the left blade holder 39) [FIG. 6C]. The analogous is related to the upper end 48 of the right blade holder 44 of the right dilating portion 35, i.e., the upper end 48 of the right blade holder 44 can have the square cross-sectional configuration (FIG. 10), rectangular cross-sectional configuration (FIG. 6B) or to have a star cross-sectional configuration (not shown).

Figure 7A:
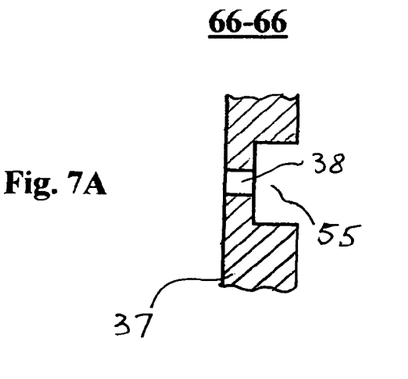
FIG. 7A is a simplified cross-sectional view 66-66 of the left knee.
Figure 7B:
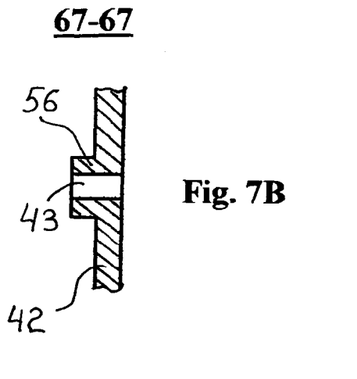
FIG. 7B is a simplified cross-sectional view 67-67 of the right knee.
Figure 7C:
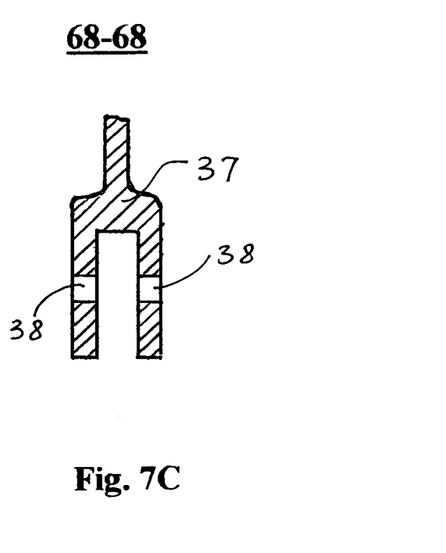
FIG. 7C is a simplified cross-sectional view 68-68 of the left knee with the U-shape configuration.
Figure 7D:
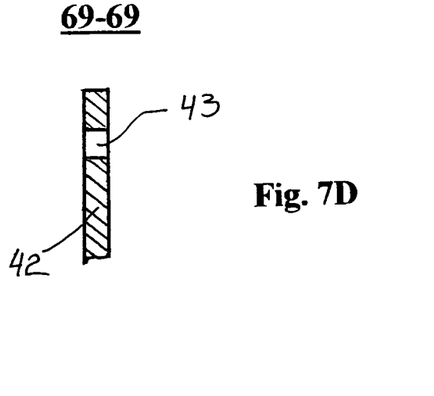
FIG. 7D is a simplified cross-sectional view 69-69 of the right knee with the straight configuration.
Figure 8:
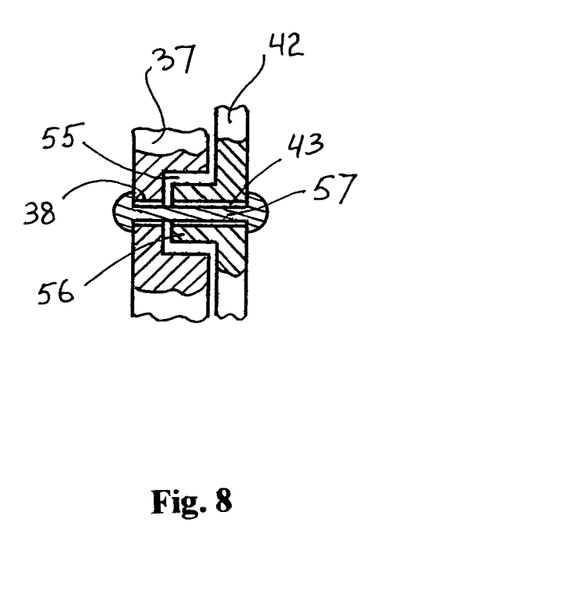
FIG. 8 is a simplified drawing of the first variant of coupling of the left dilating portion with the right dilation portion.
Figure 9:
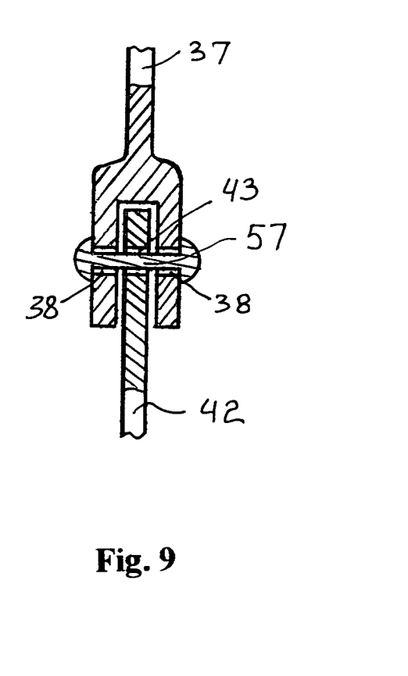
FIG. 9 is a simplified drawing of the second variant of coupling of the left dilating portion with the right dilation portion.
Figure 10:
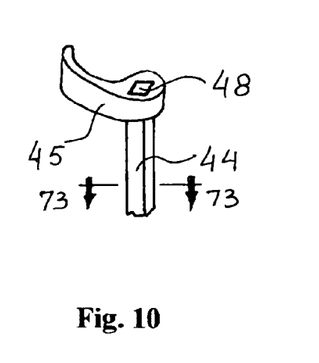
FIG. 10 is a simplified spatial view of the right blade.

The configuration of the left 37 and right 42 knees and coupling of the left knee 37 with right knee 42 are illustrated in FIGS. 7A, 7B, 8 or in FIGS. 7C, 7D, 9 depicting the U-shape (a fork-shape) of the left knee 37. As it is shown in FIG. 7A, the left knee 37 includes a recess 55. The right knee 42 comprises a right knee projection 56 (FIG. 7B), which unobstructedly fits into the recess 55 (FIG. 8). The coupling of the left knee 37 of the left dilating portion 34 with the right knee 42 of the right dilating portion 35 can be provided by the first fixing pin 57, as it is shown in FIGS. 8, 9.

According to FIG. 7C, the left knee 37 has a U-shaped knee. The right knee 42 has a straight configuration (FIG. 7D). The right knee 42 is unobstructedly fits into the "U" of the U-shaped left knee 37 (FIG. 9).

It should be understandable, that the right knee 42 can have the U-shape instead of the left knee 37 and the right knee 42 can have a recess 55 instead of the left knee 37.

The left blade holder 39 and right blade holder 44 can have any reasonable cross-sectional configuration without limitation, for example: cylindrical (hollow or solid) [not shown] or square {hollow [not shown] or solid (FIGS. 10, 12C)}, or rectangular (hollow or solid) [not shown], etc.

The star-type cross-sectional configuration of the upper ends 47 and 48 of the blade holders 39 and 44 respectively provides the adjustment of the position of the blades 41 and 45 respectively on the upper ends 47 and 48 respectively. Such adjustment can provide the convenient and secured dilating of the side walls of the vaginal opening 21, as well as the secure retaining of the width of the vaginal opening 21 during gynecological procedure.

The speculum projection 12 includes the teeth 49, intended for the rest of the cam 50 of the pawl 51, providing fixation of the handle means 19, and a third aperture 58, intended for coupling of the speculum projection 12 with the handle means extensions 59 by a second fixing pin 60 (FIGS. 14, 15B). The fixation release is provided by the fixation release trigger 20 extended from the pawl 51, as it has been mentioned hereinabove. The pawl 51 is sprung by the spring 52 (FIG. 15B). The pawl 51, including cam 50 and spring 52, is installed into the handle means 19. The fixation release trigger 20 is located on the handle means 19 in the convenient for control place, for example, as it is shown in FIGS. 3, 15B.

The left 40 and right 46 blade length adjustment means are intended to provide the convenient vertical positions of the blades 41 and 45 respectively for different vaginal canals.

The separate left 25 and right 27 cables can be presented by one solid non-separated cable (not shown), the middle of which is coupled by the cable connecting means 36 with the upper end 23 of the main cable 17.

The blades can have a permanent fixation to the blade holders or they can be dismountable, for adjustment to each different case.

The blades 41 and 45, their hooks 30 and 33 respectively, and their holders 39 and 44 respectively can be of any reasonable geometrical configuration. Also, the blades 41, 45 can be removable and can be rigidly connected to the upper ends of the blade holders 47, 48 respectively by, for example, screw 54, as it is shown in the FIG. 13.

The self-retaining vaginal retractor with a weighted speculum operates as follows.

Figure 2:
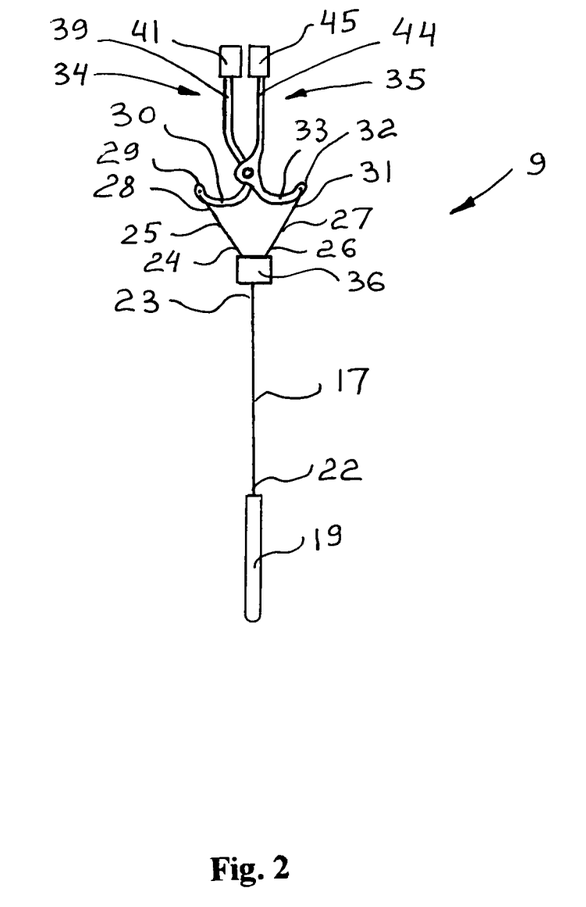
FIG. 2 is a simplified drawing of the dilating mechanism of the improved self-retaining vaginal retractor with a weighted speculum.

While the apparatus is still in the initial position, the left 41, right 45 blades and a speculum blade 6 are introduced into the vaginal cavity (canal). The speculum blade 6 depresses downward the posterior (lower) vaginal wall of patients during surgery or other gynecological procedures. The handle means 19 is in the initial position under maximal angle "β" from the lower portion 11 of the speculum 4 (FIG. 3). The left 41 and right 45 blades are also in the initial position, i.e., the blades 41 and 45 are in maximal proximity to each other (FIG. 2).

The person, providing the gynecological surgical or examination procedure, presses by hand the handle means 19 toward the lower portion 11 of the speculum body 5. The fixing means 53 automatically will fix the final pressed position, i.e.: the cam 50 of the pawl 51 will rest on the appropriate tooth of the speculum projection 12, and held the handle means 19 in that position by the appropriate tooth and spring 52 (herein the "final pressed position" means any position when the hand stop to press the handle means 19).

At the time of pressing the handle means 19, the handle projection 18 pulls the main cable 17 coupled with the lower end 22 of the main cable 17. The main cable 17 directed by the tubular means 8 pulls downward the left 25 and right 27 cables. The cables 25 and 27 pulls downward the left 30 and right 33 hooks of the left dilating portion 34 and right dilating portion 35 respectively, thereby providing pivotable movements of the dilating portions 34, 35. The left dilating portion 34 moves in the counter clockwise direction and the right dilating portion 35 moves clockwise direction, thereby, increasing the distance between the blades 41 and 45 respectively. The pressing of the handle means 19 is continued until the blades 41 and 45 will not dilate the vaginal opening 21 to the convenient width of the vaginal opening 21 for further gynecological procedure.

After the gynecological procedure is completed, the person, provided the gynecological surgical or examination procedure, holding by hand the handle means 19 (sometimes slightly pressing the handle means) releases by the free finger the fixation release trigger 20. The handle means 19, held by hand during the activated fixation released trigger 20, loosens in the person's hand and returns in its initial position at the maximal angle "n" under activity of the handle means auxiliary spring 61 (FIG. 3) inserted between the handle means 19 and lower portion 11 of the speculum body 5 of the weighted speculum 4.

Also, the return of the handle means 19 in its initial position at angle "β", for example, can be provided by the auxiliary spring 61, for example located (not shown) in the cable connecting means 36 and pulling the main cable 17 upwardly (not shown).

The angle "β" can be in the range approximate of 0°-30° and practically may not exceed of the approximate range of 0°-45°. The dilating of the vaginal opening can be regulated by the predetermined relation of the sizes (width) of the hooks and the length of the blade holders. The wider (longer) hooks, the wider vaginal opening can be provided. The longer blade holders, the wider vaginal opening can be provided. Thus, these sizes should be in the reasonable relation to each other to provide the safe for the patients and convenient for the gynecologists operation of the improved self-retaining vaginal retractor with a weighted speculum.

The length of the left 39 and right holders 44, and thereby the positions of the left 41 and right 45 blades, can be provided not by the retraction principles (FIGS. 11C and 11D), but, as it was mentioned hereinabove, by rotating of the threaded (not shown) portions of the blade holder, if the cross-section of the holder is cylindrical (not shown). For example, counter clockwise rotation of the blade holder will increase the length of the blade holder, but the clockwise rotation of the blade holder will decrease the length of the blade holder. The fixation of the desired position can be provided, for example, by the appropriate groove (not shown) along the thread of the rotating portion and the fixing screw (not shown) in the motionless threaded portion. Also, the length adjustment means can be provided, for example, by the well known left thread and right thread sliding nuts (not shown) in the swivel union (not shown), etc.

It is understandable, that the geometrical configurations of the parts (means/components, etc.) of the improved self-retaining vaginal retractor with a weighted speculum, are shown conditionally, and can be of any reasonable configuration(s) and dimension(s).

Also it should be understood, that there can be any reasonable quantity of the tubular means, tubular holders, screws, fixing and releasing means, apertures, etc.

The handle means 19 can be of any regular geometric configuration or any reasonable irregular configuration and form (not shown). The same should be understood with respect to the other components (means/parts, etc.).

It should be understandable, that there is no exact scale of the components/means from one figure to another considering sometimes necessity of the additional magnification of the details, etc.

Some appropriate means/components in the improved self-retaining vaginal retractor with a weighted speculum can be interchangeable (e.g., blades, blade holders, weighted speculums, etc.).

The material, used for the parts of the improved self-retaining vaginal retractor with a weighted speculum, can be of any reasonable but safe for health materials, e.g.; the blades can be made of the surgical steel or other suitable materials, the blade holders can be made also from the surgical steel, etc.

Thus, significant cost savings from elimination of the expensive equipment and materials are readily obtained. The improved apparatus inevitably provides the unrestricted and unobstructed visibility of and access to the vaginal canal for requiring surgical and/or examination gynecological procedure.

CONCLUSION, RAMIFICATION AND SCOPE

Accordingly, the reader will see that, according to the invention, an improved self-retaining vaginal retractor with a weighted speculum is provided. There has thus been outlined, rather broadly, the more important features of the invention. In this respect, it is understood that the invention is not limited in its application to the details of arrangements of the components/means set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not construed as limitations on the scope of the invention, but as exemplification of the presently-preferred embodiments thereof. Many other ramifications are possible within the teaching to the invention. For instance, the improved apparatus can be fully and successfully used not only for gynecology, but also in the medical areas other than gynecology, where the improved self-retaining dilating retractor is applicable for the medical procedures for the human body external openings (cavities). Also, the improved self-retaining dilating retractor can be fully and successfully used for the dilating external openings of the animal bodies in the veterinarian procedures on the animals.

The persons of ordinary skills and/or creativity in the art will readily observe that numerous modifications and advantages of the improved apparatus may be made while retaining the teachings of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

As such, those skilled in the art will appreciate that the conception, upon which this disclosure is based, can readily be utilized as a basis for the designing of other structures, for carrying out the several purpose of the present invention. It is important, therefore, that the claims be regarded as including such equivalent constructions insofar as they do not depart from the spirit and scope of the present invention.

What is claimed is:

1. A self-retaining vaginal retractor with a weighted speculum comprising
 a speculum body of said weighted speculum including
  a speculum blade extended from said speculum body;
  a middle portion, and a tubular means extending from said middle portion;
  a swollen portion extended from said middle portion;
  an elongated lower portion extended from said swollen portion;
  a speculum projection extending from said swollen portion, wherein said speculum projection includes teeth;
 a handle means including a handle projection and coupled by a fixing means with said speculum projection, wherein said fixing means comprises
  a pawl sprung by a spring and including a cam located on one side of said pawl, wherein said cam rests on a tooth of said teeth;
  a fixation release trigger located on another side of said pawl and extended outside of said handle means, wherein said pawl is coupled with said handle means by a second pin located between handle means extensions, and wherein said handle means is pivotable around said second pin;

an auxiliary spring located between said handle means and said middle portion of said speculum body, said auxiliary spring biased to return said handle means to an initial position;

a dilating mechanism of said self-retaining vaginal retractor with said weighted speculum, wherein said dilating mechanism includes a left dilating portion comprising a left hook comprising a free end;

a left knee comprising a first aperture and a recess;

a left blade holder comprising an upper end coupled with a left blade;

a right dilating portion coupled by a first pin with said left dilating portion, wherein said right dilating portion comprises a right hook comprising a free end;

a right knee comprising a second aperture and a right knee projection, which is unobstructedly inserted in said recess;

a right blade holder comprising an upper end coupled with a right blade, wherein said left dilating portion is counter clockwise pivotable around said first pin and said right dilating portion is clockwise pivotable around said first pin;

a main cable, unobstructedly passing through said tubular means, and a lower end of which is coupled with said handle projection, wherein an upper end of said main cable is by a cable connecting means coupled with a first end of a left cable and with a first end of a right cable, and wherein a second end of said left cable is coupled with said free end of said left hook and a second end of said right cable is coupled with said free end of said right hook.

2. The self-retaining retractor of claim 1, wherein further said tubular means is coupled with said middle portion of said speculum body by an upper tubular holder and a lower tubular holder.

3. The self-retaining retractor of claim 1, wherein further said auxiliary spring is located in said cable connecting means.

4. The self-retaining retractor of claim 1, wherein further said left blade is removable and fixable to said upper end of said left blade holder and said right blade is removable and fixable to said upper end of said right blade holder.

5. The self-retaining retractor of claim 1, wherein further said left blade holder includes a left blade length adjustment means and said right blade holder includes a right blade length adjustment means.

6. The self-retaining retractor of claim 1, wherein further said right dilating portion includes said right knee having a straight configuration and said left dilating portion includes said left knee having a U-shaped configuration, wherein said straight right knee is unobstructedly inserted in said U-shape of said left knee.

7. The self-retaining retractor of claim 1, wherein further said left dilating portion includes said left knee having a straight configuration and said right dilating portion includes said right knee having a U-shaped configuration, wherein said straight left knee is unobstructedly inserted in said U-shape of said right knee.

\* \* \* \* \*